(12) United States Patent
Trevisiol et al.

(10) Patent No.: US 7,517,538 B2
(45) Date of Patent: *Apr. 14, 2009

(54) SOLID SUPPORTS FUNCTIONALISED WITH PHOSPHORUS DENDRIMERS, METHOD FOR PREPARING SAME AND USES THEREOF

(75) Inventors: Emmanuelle Trevisiol, Cornebarrieu (FR); Julien Leclaire, Toulouse (FR); Geneviève Pratviel, Toulouse (FR); Anne-Marie Caminade, Toulouse (FR); Jean Francois, Castenet (FR); Jean-Pierre Majoral, Ramonville (FR); Bernard Meunier, Castenet (FR)

(73) Assignees: Centre National de la Recherche Scientifique (FR); Institut National de la Recherche Agronomique (FR)

( * ) Notice: Subject to any disclaimer, the term of this patent is extended or adjusted under 35 U.S.C. 154(b) by 243 days.

This patent is subject to a terminal disclaimer.

(21) Appl. No.: 10/512,133

(22) PCT Filed: Apr. 17, 2003

(86) PCT No.: PCT/FR03/01231

§ 371 (c)(1),
(2), (4) Date: May 25, 2005

(87) PCT Pub. No.: WO03/091304

PCT Pub. Date: Nov. 6, 2003

(65) Prior Publication Data

US 2005/0214767 A1    Sep. 29, 2005

(30) Foreign Application Priority Data

Apr. 23, 2002 (FR) ................... 02 05049

(51) Int. Cl.
 A61K 9/14    (2006.01)
 C12Q 1/68    (2006.01)
 C07H 21/00   (2006.01)
 A61K 43/04   (2006.01)
 G01N 15/06   (2006.01)
(52) U.S. Cl. .................. 424/486; 435/6; 435/455; 536/25.3; 422/68.1; 514/44
(58) Field of Classification Search ............... 536/25.3; 435/6, 455; 422/68.1; 424/486; 514/44
See application file for complete search history.

(56) References Cited

U.S. PATENT DOCUMENTS 6,455,071 B1 * 9/2002 Shchepinov et al. ........ 424/486

FOREIGN PATENT DOCUMENTS

EP    2 801 592 A1    6/2001

(Continued)

OTHER PUBLICATIONS

Turrin et al., "Organic-Inorganic Hybrid Materials Incorporating Phosphorus-Containing Dentrimers", Chem. Mater., 2000, 12, pp. 3848-3856.

(Continued)

Primary Examiner—Jezia Riley
(74) Attorney, Agent, or Firm—Alston & Bird LLP

(57) ABSTRACT

The present invention relates to solid supports functionalized with phosphorus-containing dendrimers, to a process for preparing them, to their use for preparing biochips and to the uses of these biochips, in particular for immobilizing molecules of interest, especially biological molecules of interest such as nucleic acids, polypeptides, lipids and proteins.

15 Claims, 7 Drawing Sheets

FOREIGN PATENT DOCUMENTS

| | | |
|---|---|---|
| WO | WO 00/55627 | 9/2000 |
| WO | WO 01/51689 A1 | 7/2001 |

OTHER PUBLICATIONS

Soler-Illia et al., "New Mesotextured Hybrid materials Made from Assemblies of Dendrimers and Titanium (IV)-Oxo-Organo Clusters", *Angew. Chem. Int. Ed.*, 2000, 39 No. 23, pp. 4250-4254.

Maraval et al., "Varying Topology of Dendrimers—A New Approach toward the Synthesis of Di-Block Dendrimers", *Eur. J. Inorg. Chem.*, 2001, pp. 1681-1691.

Benters et al., "Dendrimer-Activated Solid Supports for Nucleic Acid and Protein Microarrays", *Chembiochem*, 2001, 2, pp. 686-694.

Maraval et al., "Rapid Synthesis of Phosphorus-Containing Dendrimers with Controlled Molecular Architectures: First Example of Surface-Block, Layer-Block, and Segment-Block Dendrimers Issued From the Same Dendron", *American Chemical Society*, 2000, 122, pp. 2499-2511.

Galliot et al., "Regioselective Stepwise Growth of Dendrimer Units in the Internal Voids of a Main Dendrimer", www.sciencemag.org, vol. 277, Sep. 26, 1997, pp. 1981-1984.

* cited by examiner

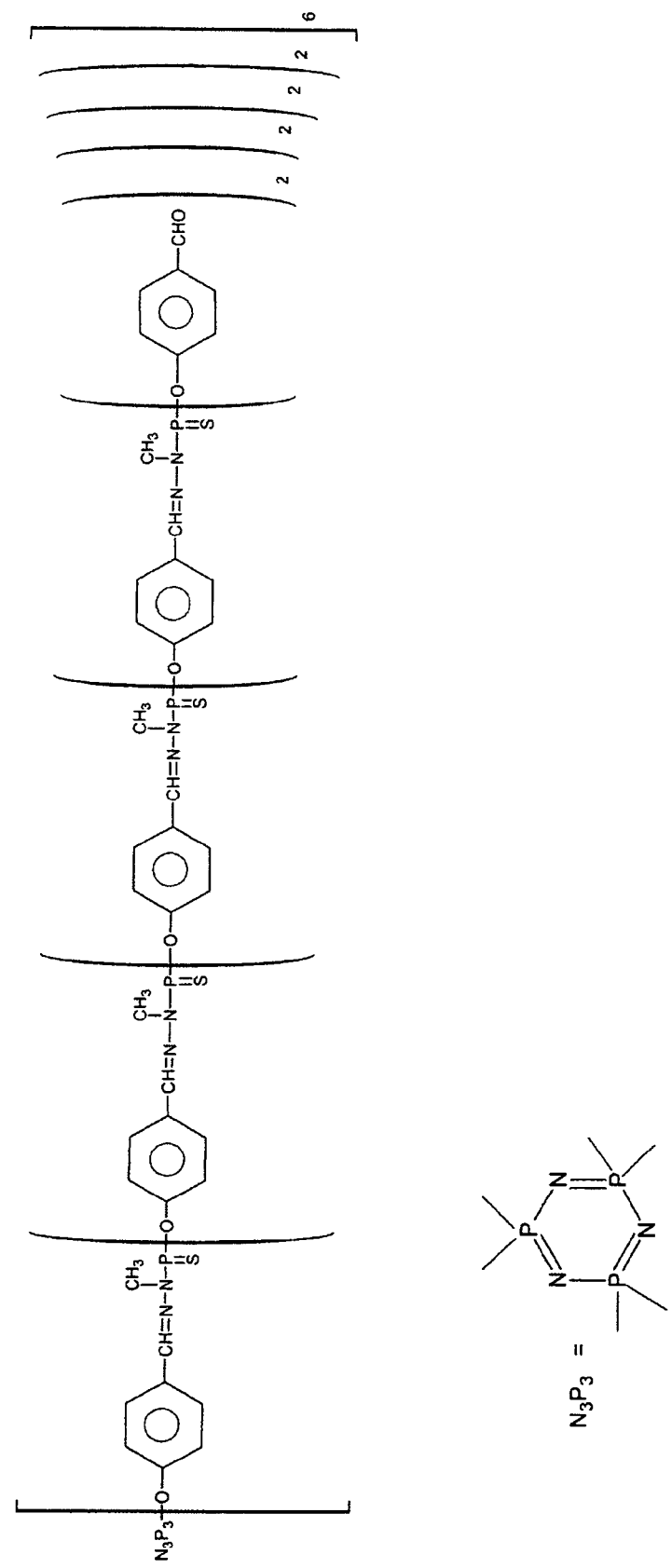
FIGURE 2
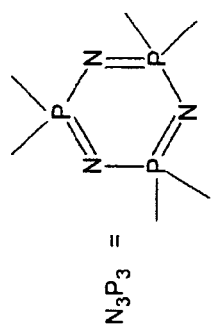

SOLID SUPPORTS FUNCTIONALISED WITH PHOSPHORUS DENDRIMERS, METHOD FOR PREPARING SAME AND USES THEREOF

The present invention relates to solid supports functionalized with phosphorus-containing dendrimers, to a process for preparing them, to their use for preparing biochips and to the uses of these biochips, in particular for immobilizing macromolecules, especially biological macromolecules such as nucleic acids, lipids, proteins (peptides, enzymes, antibodies, etc.) or molecular partners thereof.

The exponential development of genomics and pharmacogenomics related to the sequencing not only of the human genome but also to that of animals, bacteria, viruses, plants, etc. is leading academic or industrial research laboratories to consume enormous amounts of reliable biochips that are easy to manufacture.

Now, in this particular context, it is of prime importance to have available functionalized solid supports that have a certain number of qualities.

These supports must in particular allow the reproducible immobilization of molecules of interest, since reproducible immobilization is conditional for detection that is itself reproducible.

These supports must also allow the immobilization of the molecules of interest in a sensitive manner. The sensitivity of a functionalized solid support depends on the degree of immobilization and on the method for detecting a signal, but also and above all on the level of background noise (nonspecific signal). A reduction in the background noise improves the signal/noise ratio. Specifically, in a device in which the presence of biological species in the region of the surface is detected, the background noise comes essentially from the nonspecific adsorption of molecules, including labeled biological molecules of interest, and should consequently be limited. The ideal is thus to obtain a support that has a very low background noise and a high signal detection intensity.

Moreover, and especially in the particular case of hybridization reactions using nucleic acids, the attachment of probes to the surface of a solid support should ensure the integrity of the sequence and the stability of the deposit. After the hybridization step, the results should be reproducible from one support to another. To this end, the probes should be spaced out on the surface of the solid support, so as not to disrupt the hybridization with the target nucleic acids. This makes it possible to come close to the solution hybridization conditions by mimicking a three-dimensional hybridization rather than a two-dimensional hybridization conventionally obtained via a glass-slide technique. A spacer of at least about 40 atoms (4-5 nm) is necessary to avoid the steric constraints between the DNA and the surface of the support.

Moreover, it is important to have available reusable functionalized solid supports. The possibility of having available a reusable support is of major interest since it permits the analysis of several biological samples with the same device, thus making it possible to make quantitative comparisons. Furthermore, the reusable supports enable several measurements to be taken on the same sample and thus allow a statistical improvement in the results.

At the present time, various types of processes for preparing biochips have already been proposed.

Biochips, and in particular nucleic acid biochips, may be manufactured either by in situ synthesis or by immobilization of probes.

In the first case (in situ synthesis), the probes are oligonucleotides, which are synthesized step by step directly on the support, and which are generally between 20 and 30 bases in size. This manufacturing process allows access to high-density chips (McGall et al, J. Am. Chem. Soc., 1997, 119, 5081-5090).

In the second case (immobilization of probes), the probes are presynthesized and then immobilized on the support. Two types of interactions with the surface may then take place.

The probe nucleic acid may be maintained on the surface by means of electrostatic interactions between the phosphate groups of the negatively charged skeleton and the modified surface of the positively charged support. By way of example, this type of biochip may be obtained by covering the surface with poly-L-lysine or by silanization with an aminosilane (Zammatteo et al, Anal. Biochem., 2000, 280, 143-150; Eisen et al, Methods in Enzymol, 1999, 303, 179-205). In this type of immobilization, the probe is generally coated onto the support, which may lead to problems of accessibility during the hybridization step. Furthermore, ionic interactions of this type are not sufficiently stable to allow reuse of the biochip.

The probe nucleic acid may also be grafted onto the support by means of covalent interactions. Generally, the bonds between the probes and the support are established at either the 3' or 5' end of the nucleic acid, allowing accessibility of the probe over its entire length, resulting in better quality of response in terms of hybridization. Several combinations of functionalization of the support and of the nucleic acids may be encountered. For example, the support may comprise nucleophilic functions such as —$NH_2$ or —SH functions and the nucleic acid to be grafted may then comprise an electrophilic function, for instance a —CHO, —NCS, —NHS or —COOR function, and vice versa. According to another variant, the support and the nucleic acid may be nucleophilic and a di-electrophilic spacer will allow coupling between the two species. Finally, the support and the probe may be electrophilic and the coupling will be achieved by means of a di-nucleophilic spacer.

The biochips currently manufactured are, for the very large part, made using glass as support.

The biochips most frequently used have surfaces functionalized with a spacer ending with an —$NH_2$ function. Their efficacy in terms of attachment and hybridization has been confirmed, but no reuse of this type of slide is possible, since the interactions between the probes and the support are of ionic type.

Other slides comprising aldehyde functions on their surface are marketed. These functions are introduced by using a silane-aldehyde, a simple spacer, which has only one anchoring function per molecule, whether it be on the support side or on the nucleic acid side. It has been shown that anchoring via several points to the surface is important (Zhao et al., Nucl. Acids Res., 2001, 29, 955-959; international patent application WO 01/51689) since it allows an increase in the sites of binding of the probes to the support, which results in a better response in terms of hybridization.

Another way of obtaining better detection sensitivity is reported especially in the studies by M. Beier and J. D. Hoheisel, Nucl. Acids Res., 1999, 27, 1970-1977. The authors constructed, on a glass slide, branched molecules containing six branches, with the aim of increasing the probe density. The nature of these branched spacers also makes it possible to modify the hydrophilic or hydrophobic nature of the surface. Their preparation process includes eight synthetic steps in total, starting from an amino slide, to obtain the biochip, which greatly limits their industrial development. Furthermore, the branched molecules are generated in situ in an uncontrollable manner, and their structure is not defined, which does not make it possible to ensure homogeneity of the surface of the biochip thus obtained. Since all the bonds are covalent, the authors have shown that their biochips could be reused. It should be noted that the reuse of biochips is common in the case of a Nylon® support and has more recently been described with plastic (see international patent application WO 00/55627).

Finally, recent studies (Benters et al, Chembiochem., 2001, 2, 686-694) describe the use of "PAMAM® starburst" amino dendrimers for the manufacture of biochips, seven synthetic steps that are demanding in terms of operating conditions, and of which some cannot be controlled since they are performed directly on the glass, for the production of a support that is not stable over time. Specifically, the use of these biochips includes a step of preactivation of the dendrimer layer before forming the coupling with the oligonucleotides. This step generates a reactive surface that is not stable over time, since the authors indicate that the probes must be grafted immediately after activation. This greatly limits the marketing of this type of support.

The exponential development of genomics and pharmacogenomics related to the sequencing not only of the human genome, but also to that of animals, bacteria, viruses, plants, etc. is leading academic or industrial research laboratories to consume enormous amounts of reliable biochips that are easy to manufacture. Reuse is an additional criterion that makes it possible to statistically validate biological tests. It is therefore in order to remedy all of these drawbacks and to have available reusable biochips that may be manufactured at low cost, in few steps, controllably and reproducibly, and that have excellent stability and very good detection sensitivity, that the Inventors have established the development that is the subject of the invention.

A first subject of the present invention is thus a solid support, characterized in that it comprises at least one surface covalently functionalized with phosphorus-containing dendrimers having a central core that contains at least two functional groups and comprising at their periphery several functions capable of allowing the binding of said dendrimers to said surface and also the binding or the in situ synthesis of molecules of interest, said dendrimers being between 1 and 20 nm in size.

In the description hereinbelow, such solid supports functionalized with phosphorus-containing dendrimers are referred to as "dendrislides".

Dendrimers are isomolecular polymers of defined branched structure, formed from a central core from which branches are created or grafted. These branches are multifunctional, i.e. they bear, in particular at the periphery, several identical or different functional chemical groups, chosen according to the properties that it is desired to give to the dendrimer. Each new generation is obtained by introducing a new level of branching. The set of junction points of the branches located an equal distance from the core corresponds to a generation. A schematic representation of a generation 4 dendrimer, obtained from a trifunctional core, is given in the attached FIG. 1.

Among the dendrimers that may be used according to the invention, the preferred ones are those consisting of:

a central layer in the form of a central core $P_0$, optionally containing phosphorus, comprising from 2 to 12 functionalized groups, n intermediate layers, which may be identical or different, each of said intermediate layers consisting of $P_1$ units corresponding to formula (I) below:

$$L-M-\underset{R_1}{C}=N-\underset{R_2}{N}-P\underset{E}{\overset{\diagup}{\underset{\diagdown}{\|}}} \quad (I)$$

in which:

L is an oxygen, phosphorus, sulfur or nitrogen atom,

M represents one of the following groups:

an aromatic group di-, tri- or tetrasubstituted with alkyl groups, alkoxy groups, unsaturated groups of the $C_1$-$C_{12}$ olefinic, azo or acetylenic type, all these groups possibly incorporating phosphorus, oxygen, nitrogen or sulfur atoms or halogens, or an alkyl or alkoxy group comprising several substituents as defined when M is an aromatic group, $R_1$ and $R_2$, which may be identical or different, represent a hydrogen atom or one of the following groups: alkyl, alkoxy, aryl, optionally comprising phosphorus, oxygen, sulfur or nitrogen atoms or halogens with $R_2$ usually being different than $R_1$, n is an integer between 1 and 11, E is an oxygen, sulfur or nitrogen atom, said nitrogen atom possibly being linked to an alkyl, alkoxy or aryl group, all these groups possibly incorporating phosphorus, oxygen, nitrogen or sulfur atoms or halogens, an external layer consisting of units $P_2$, which may be identical or different, and corresponding to formula II below:

$$-[W-X] \quad (II)$$

in which:

W represents one of the following groups: alkyl, alkoxy, aryl, all these groups possibly comprising phosphorus, oxygen, nitrogen or sulfur atoms or halogens, X represents an aldehyde, thiol, amine, epoxide, carboxylic acid, alcohol or phenol group, and more generally any group possibly comprising phosphorus, oxygen, nitrogen, sulfur, carbon or halogen atoms.

Preferably, the central core $P_0$ of these dendrimers is selected from the group consisting of the group of general formula IIIa:

$$\text{(IIIa)}$$

and the group of general formula IIIb:

$$R_5=P\underset{\diagdown}{\overset{\diagup}{-}} \quad \text{(IIIb)}$$

in which $R_5$ represents a sulfur, oxygen or nitrogen atom.

According to one advantageous embodiment of the invention, the dendrimers are chosen from compounds in which the group of formula (I) above represents the following group:

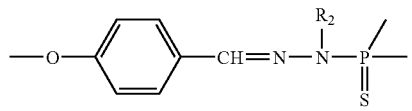

in which $R_2$ represents a $C_1$-$C_{12}$ alkyl radical and more particularly a methyl radical;

and the group of formula (II) represents one of the following two groups:

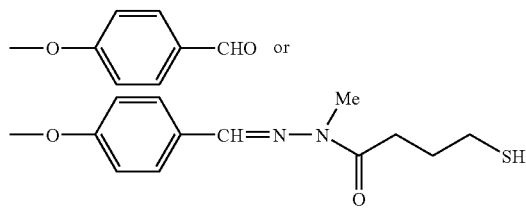

and in which the number of generations preferably ranges between 1 and 6.

Examples of such dendrimers are given in the attached FIGS. 2 and 3, which represent, respectively, the structure of a generation 4 dendrimer containing aldehyde end groups and the structure of a generation 3 dendrimer containing thiol end groups.

Among the solid supports that may be functionalized in accordance with the invention, mention may be made in particular of supports comprising at least one siliceous surface such as glass slides, beads and capillaries, silicon or plastic supports and metallic supports, for instance gold terminals.

The dendrimers used in accordance with the invention may be synthesized in a manner known to those skilled in the art, by repetition of a reaction sequence allowing the production of a new generation at the end of each synthetic cycle and consequently of an increasing number of branches and of peripheral functions that are all identical (Tomalia D. A., Ang. Chem. Int. Ed., 1990, 29, 138; Launay et al, Angew. Chem. Int. Ed. Engl., 1994, 33, 1589 and J. Organomet. Chem., 1997, 529, 51).

In particular, these dendrimers may be constructed stepwise from a central core containing at least two functional groups, for example hexachlorocyclotriphosphazene: $N_3P_3Cl_6$, which contains six functional groups.

More specifically, these dendrimers are generally constructed by the repetition of two steps starting from the core. The first step is the substitution of chlorine atoms in basic medium with a difunctional compound containing an alcohol function and an aldehyde function, for example 4-hydroxybenzaldehyde. The second step creates the branching points and consists of a condensation reaction with a compound containing two types of function: an $NH_2$ group and at least one $PCl_2$ group, for instance the compound $H_2NNMeP(S)Cl_2$. The first two steps of the synthetic method starting from the hexafunctional core are represented in the synthetic scheme A shown in the attached FIG. 4.

An iterative sequence of the synthetic steps makes it possible to construct dendrimers of increasing generation.

Table 1 below shows the number of terminal functions present at the periphery of the dendrimers of different generations obtained from the core $N_3P_3$, and also their size in Angströms:

TABLE I

| Generation | Number of functions | Size (A) |
| --- | --- | --- |
| 1 | 12 | 30 |
| 2 | 24 | 45 |
| 3 | 48 | 60 |
| 4 | 96 | 75 |
| 5 | 192 | 90 |
| 6 | 384 | 105 |
| 7 | 768 | 120 |

A subject of the present invention is also a process for preparing a solid support in accordance with the invention (dendrislide), characterized in that it comprises a step of forming a covalent bond between phosphorus-containing dendrimers having a central core that contains at least two functional groups, said dendrimers comprising at their periphery several functions capable of allowing their binding to said surface and the binding or the in situ synthesis of molecules of interest, and the functionalized or nonfunctionalized surface of a solid support to obtain a solid support covalently functionalized with said dendrimers.

According to a first embodiment of the process in accordance with the invention, the dendrimers comprise at their periphery functions allowing the direct attachment, by means of a covalent bond, of these dendrimers to the non-prefunctionalized surface of said solid support. This is the case, in particular, when the dendrimers comprise thiol functions at their periphery and when the solid support comprises a gold surface.

According to a second embodiment of the process in accordance with the invention, and when the surface of the solid support used does not comprise any functions compatible with the peripheral functions of the dendrimer used, it is then necessary to prefunctionalize said surface with functions capable of allowing the covalent binding of said dendrimers.

According to this second variant, the process in accordance with the invention is then characterized in that it comprises the following steps:

a) the functionalization of at least one surface of a solid support with functions capable of allowing the binding of phosphorus-containing dendrimers having a central core that contains at least two functional groups, said dendrimers comprising at their periphery several functions capable of allowing their binding to said surface thus functionalized and the binding or the in situ synthesis of molecules of interest;

b) the optional preactivation of the functions of the support to obtain an activated functionalized surface, c) the formation of a covalent bond between said dendrimers and said functionalized and optionally activated surface, to obtain a solid support covalently functionalized with said dendrimers.

According to one advantageous embodiment of the invention, the step a) of functionalization of the surface of the solid support is performed by silanization using a silanization reagent comprising functions capable of binding dendrimers, for instance amine groups.

By way of example, the silanization step may be performed using an amino silanization reagent, for instance 3-aminopropyltriethoxysilane (sigma), aminopropyldiethoxymethylsilane or aminopropylmonoethoxydimethylsilane.

According to one preferred embodiment of the invention, the step of direct covalent binding of the dendrimers (the case of the first variant) and the step a) of silanization of the surface of the support (the case of the second variant) are preceded by a step of cleaning the surface of the support in basic, acidic and/or oxidizing medium.

In the particular case of the second variant of the process in accordance with the invention, these two steps of washing and silanization are summarized in the synthetic scheme B below:

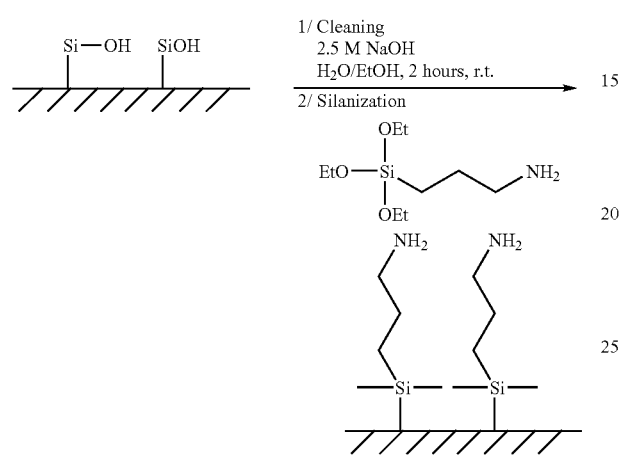

The optional preactivation step b) serves to reactivate, if necessary, the amine functions bound to the support after the silanization step. Specifically, storage, even for a short while, of the amino solid supports may result in protonation of the $NH_2$ groups. It is thus often preferable to reactivate the amine functions in basic medium before reacting the dendrimers. In this particular case, steps b) and c) are represented in Scheme C below:

SCHEME C b) Preactivation

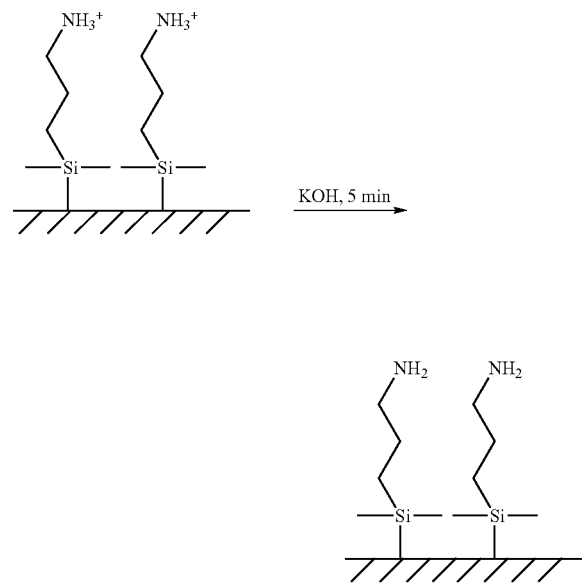

c) Fonctionalization with the dendrimers

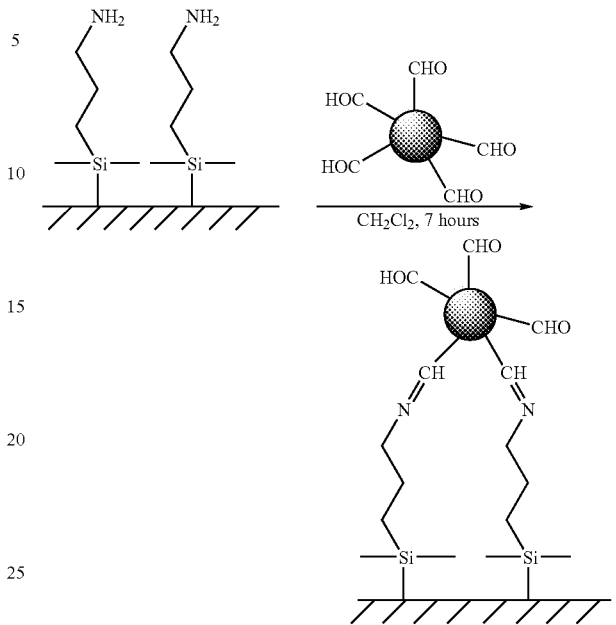

According to one advantageous embodiment of the process in accordance with the invention, this preactivation step is performed by treating the support with a basifying agent for instance potassium hydroxide, for a period of between about 2 and 20 minutes.

According to one advantageous embodiment of the invention, the step of covalent binding of the dendrimers consists in:

preparing a solution of said dendrimers in a solvent, for instance dichloromethane or tetrahydrofuran, placing said dendrimer solution in contact with the optionally functionalized and optionally activated surface, for a period of between about 10 minutes and 24 hours, preferably between about 2 and 8 hours, at a temperature preferably of between about 4 and 50° C.

After the step of covalent binding of the dendrimers, the supports in accordance with the invention (dendrislides) are preferably rinsed and then dried.

The rinsing step is preferably performed using an organic solvent such as dichloromethane or tetrahydrofuran, and then using a lower alcohol such as ethanol.

The drying of the dendrislides may be performed, for example, in compressed air, under a stream of nitrogen or by centrifugation.

The dendrislides thus obtained may then be stored and/or used directly for the immobilization and/or in situ synthesis of molecules, in particular of biological molecules.

The dendrislides in accordance with the invention may in particular be stored for at least two months, without any impairment occurring in the functions located at the periphery of the dendrimers.

A subject of the present invention is thus also the use of a solid support functionalized with phosphorus-containing dendrimers in accordance with the invention (dendrislides), as a support for the immobilization and/or in situ synthesis of molecules of interest, for instance nucleic acid molecules (oligonucleotides, PCR products, etc.), lipids, proteins (peptides, enzymes, antibodies, etc.) or molecular partners thereof.

A subject of the invention is also a biochip, characterized in that it consists of a solid support comprising at least one surface functionalized with phosphorus-containing dendrimers, onto which are covalently bound molecules of interest such as nucleic acids (oligonucleotides, PCR products, etc.), lipids, proteins (peptides, enzymes, antibodies, etc.) or molecular partners thereof.

According to the invention, such biochips are referred to as "dendrichips".

Such dendrichips have a very low background noise and a high signal intensity, for example after hybridization of nucleic acids with fluorescent targets. These "dendrichips" have the advantage of being reusable without any significant loss of the signal, but above all without any increase in the background noise. This results in a significant reduction in the analysis costs and makes it possible to obtain reliable statistical data for a given analysis. Furthermore, these dendrichips are obtained in a few synthetic steps (3 to 5); these steps proceed under non-constraining operating conditions, in a controlled and reproducible manner.

Moreover, by virtue of the very structure of the dendrimers, these dendrichips may have the advantage of having multiple points of attachment to the surface, on the one hand, and to the molecules of interest, on the other hand, the whole ensuring excellent stability of the support-dendrimers-molecules of interest assembly.

Another subject of the invention is a process for preparing a dendrichip as defined above, characterized in that it consists in placing a solid support, containing at least one surface functionalized with phosphorus-containing dendrimers comprising at their periphery functions capable of allowing the covalent binding of molecules of interest, in contact with a buffer solution containing molecules of interest that have been prefunctionalized with, or that already comprise, one or more groups capable of forming a covalent bond with said peripheral functions of the dendrimers.

According to a first embodiment of this process, and when the peripheral functions of the dendrimers used are aldehyde functions, then the molecules of interest are preferably prefunctionalized with, or already contain, one or more amine functions, or are prefunctionalized with one or more oxyamine (—ONH$_2$) or hydrazine (—NH—NH$_2$) functions, and more generally with any function capable of reacting with an aldehyde function.

Also, in this case, the molecules of interest (amino nucleic acids, oligonucleotides of variable sizes or PCR products) are deposited on the "dendrislides" using, for example, 0.3 M pH 9 phosphate buffer. When the molecules of interest are prefunctionalized with, or already contain, one or more amine functions, this step is followed by a reduction of the imine functions present between the nucleic acids and the dendrimers, on the one hand, and between the dendrimers and the support, on the other hand (see scheme D below). This reduction step also makes it possible to reduce the residual aldehyde functions to alcohol, making the surface hydrophilic. Furthermore, the alcohols cannot result in any nonspecific reaction with the labeled targets (no increase in the background noise).

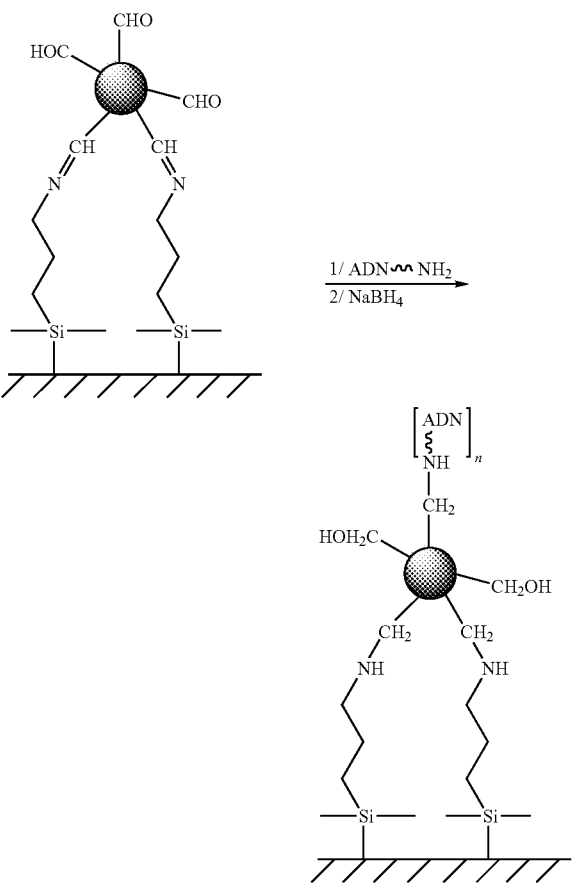

SCHEME D

According to a second embodiment of this process, and when the peripheral functions of the dendrimers used are thiol functions, then the molecules of interest are preferably prefunctionalized with, or already contain, one or more thiol functions (to allow the creation of a disulfide bridge), or are prefunctionalized with one or more iodoacetamido (—NHCO—CH$_2$—I) functions, and more generally with any function capable of reacting with a thiol function. This type of functionalization is particularly suitable for solid supports comprising a surface of silicon or gold type. In the case of a disulfide bond established between the support and the nucleic acid probes, the surface may be regenerated by means of a reduction step. The thiol surface thus obtained may again be "recharged" with other oligonucleotide sequences or with proteins.

According to a third embodiment of this process, and when the peripheral functions of the dendrimers used are amine functions, then the molecules of interest are prefunctionalized with, or already contain, one or more aldehyde, α-oxoaldehyde, —COOR, —NCS or —NHS functions, and more generally with any function capable of reacting with an amine function.

According to a fourth embodiment of this process, and when the peripheral functions of the dendrimers used are epoxide functions, then the molecules of interest are prefunctionalized with, or already contain, one or more amine functions, and more generally any function capable of reacting with an epoxide function.

According to the process for preparing the dendrichips in accordance with the invention, the reaction for the covalent binding of the molecules of interest to the dendrislides is preferably performed at a temperature of between about 4 and 50° C., for a period of between about 2 and 24 hours.

The dendrichips thus obtained may advantageously be used as miniaturized diagnostic tools, depending on the nature of the bound molecules of interest, for example as DNA chips to perform hybridization reactions with complementary targets, or as peptide, polypeptide or protein chips, for example, for the detection of responses of antigen-antibody type by means of using labeled, fluorescent, radioactive or chemically labeled reagents.

The dendrichips in accordance with the present invention may also be used as polypeptide chips for screening molecules and for analysis of the relationships between molecules, of ligand-receptor type.

Such dendrichips in particular have the advantage of being reusable.

In addition to the preceding arrangements, the invention also comprises other arrangements, which will emerge from the description that follows, which refers to two examples of the preparation of glass dendrislides functionalized with dendrimers of different generations and containing aldehyde ends, to an example of the preparation of biochips from these dendrislides, to an example of immobilization of nucleic acid molecules on biochips in accordance with the invention, to an example of synthesis of a third generation dendrimer containing thiol ends, and to an example of the preparation of dendrislides with third generation dendrimers containing thiol ends, and also to FIGS. 1 to 7 in which:

FIG. 2 is the formula of a fourth generation phosphorus-containing dendrimer comprising aldehyde-terminal peripheral functions;

EXAMPLE 1

Figure 1:
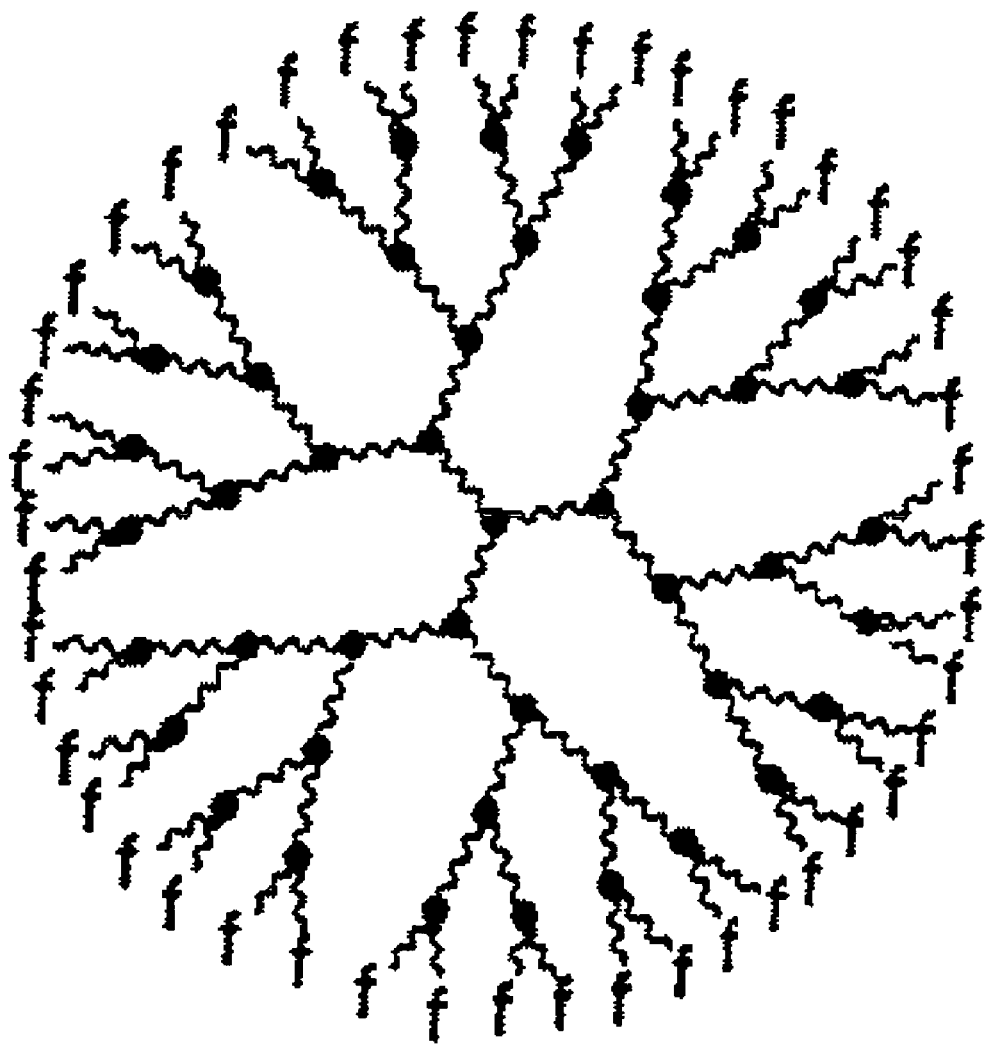
FIG. 1 is a schematic view of a fourth generation dendrimer, obtained from a trifunctional core.

Preparation of a Solid Support Consisting of a Glass Slide Functionalized with Phosphorus-Containing Dendrimers Containing Aldehyde end Groups (Dendrislides)

1) First Step: Preactivation of the Glass Slides

Commercial glass slides, functionalized with amine groups (CORNING®-CMT-GAPS Amino-Silane Coated Slides) are immersed in an aqueous potassium hydroxide solution (8%) for 20 minutes with agitation using an orbital shaker at a speed of 30 rpm (Heidolph Instruments Polymax 1040). The slides are then rinsed thoroughly with MilliQ water (3 washes of 5 minutes each) and are finally dried under a stream of nitrogen.

2) Second Step: Preparation of the "Dendrislides"

In this example three different types of dendrimer were used:

G3 dendrimers: Third generation dendrimers comprising a phosphorus-containing core of formula (IIIa) as described above and comprising 48 aldehyde functions at their periphery;

G4 dendrimers: Fourth generation dendrimers comprising a phosphorus-containing core of formula (IIIa) as described above and comprising 96 aldehyde functions at their periphery;

G5 dendrimers: Fifth generation dendrimers comprising a phosphorus-containing core of formula (IIIa) as described above and comprising 192 aldehyde functions at their periphery.

The preactivated slides are immersed in a solution of dendrimers G3, G4 or G5 at 0.1% in dichloromethane. They are agitated for 6 hours at room temperature (30 rpm). They are then rinsed with dichloromethane (2 washes of 5 minutes each) and then with ethanol (1 wash of 5 minutes) and are finally dried under a stream of nitrogen.

Glass slides whose surface is functionalized with G3, G4 or G5 dendrimers (dendrislides: DS-A-G3; DS-A-G4 and DS-A-G5) are thus obtained. These dendrislides may then be used for the immobilization of molecules of interest.

EXAMPLE 2

Preparation of a Solid Support Consisting of a Glass Slide Functionalized with Phosphorus-Containing Dendrimers Containing Aldehyde end Groups ("Dendrislides")

1) First Step: Cleaning of the Glass Slides

Commercial glass slides (Gold-Seal-Microslides®, Polylabo) are placed in a slide holder and this holder is immersed in an alkaline washing solution consisting of 50 g of sodium hydroxide in 200 ml of MilliQ water and 300 ml of 95% ethanol. The slides are agitated for 2 hours at room temperature. They are then rinsed thoroughly with MilliQ water (3 washes of 5 minutes each) and dried under a stream of nitrogen or by centrifugation.

2) Second Step: Silanization

The glass slides thus cleaned are immersed in a solution of 3-aminopropyltriethoxysilane (GAPS, Aldrich) at 10% in 95% ethanol and are agitated overnight at room temperature. They are then left for 30 minutes in open air, rinsed with 95% ethanol (two washes of 5 minutes each) and then with MilliQ water (1 wash of 5 minutes and 1 wash of 2 minutes with sonication), and then dried under a stream of nitrogen. They are then maintained for 3 hours at a temperature of 120° C.

3) Third Step: Preactivation

The silanized slides are placed in an aqueous potassium hydroxide solution (8%) for 5 minutes, with agitation at room temperature. They are then rinsed with MilliQ water (3 washes of 5 minutes each), and then dried under a stream of nitrogen.

4) Fourth Step: Functionalization with the Dendrimers

The preactivated slides are placed in a solution of G4 dendrimers as described above in Example 1 (0.1% in dichloromethane) for 7 hours with agitation at room temperature.

They are then washed with dichloromethane (2 washes of 5 minutes each) and then with ethanol (1 wash of 5 minutes), and then dried under a stream of nitrogen.

A solid support functionalized with phosphorus-containing dendrimers containing aldehyde functions (dendrislide: DS-B-G4) is thus obtained. This dendrislide may then be used for the immobilization of molecules of interest.

EXAMPLE 3

Preparation of Biochips from the Dendrislides Prepared in Examples 1 and 2: "Dendrichips"

1) Deposition of the Oligonucleotides
a) Oligonucleotides Used
Oligonucleotide ON1: 35-mer amine having the sequence SEQ ID No 1 below:
5'-GTG-ATC-GTT-GTA-TCG-AGG-AAT-ACT-CCG-ATA-CCA-TT-3', modified in the 5' position with an —NH$_2$—(CH$_2$)$_6$— group.

This oligonucleotide, which is modified at its 5' end with a 6-carbon arm ending with an amine function (Eurogentec, Belgium) allows reaction with the aldehyde functions present on the dendrislide as described above in examples 1 and 2.

Oligonucleotide ON2: 35-mer oxyamine having the sequence SEQ ID No 1 described above and modified in the 5'position with an —H$_2$NO—(CH$_2$)$_6$—.

The sequence SEQ ID No 1 of the oligonucleotides ON1 and ON2 corresponds to a part of the gene GPH1 of the yeast *Saccharomyces cerevisiae*.

The oligonucleotides were deposited using the Eurogridder® robot (Eurogentec, Seraing, Belgium) and were spaced apart by 200 µm.

b) Deposition on the Dendrislides
The dendrislides DS-A-G3, DS-A-G4, DS-A-G5 and DS-B-G4 as prepared above in examples 1 and 2 are used.

On the slides DS-A-G3, DS-A-G4 and DS-A-G5 prepared in example 1, the oligonucleotides ON1 are deposited in a 0.3M phosphate buffer (pH 9) containing increasing amounts of dimethyl sulfoxide (DMSO) (0; 10; 20; 30; 40 or 50%, v/v) using the Eurogridder® robot (Eurogentec, Belgium). The volumes deposited are 2 nl and the concentrations range from 1 µM to 10 µm (1; 2; 5 and 10 µM). After deposition, the slides are left overnight at room temperature. They are then immersed in aqueous sodium borohydride solution (NaBH$_4$, 3.5 mg/ml) (step of reduction of the imine functions) and are agitated for 3 hours at room temperature. They are then rinsed with MilliQ water (3 washes of 5 minutes each) and are dried under a stream of nitrogen or by centrifugation. The following dendrichips (DC) are obtained: DC1-A-G3; DC1-A-G4 and DC 1-A-G5.

On the dendrislides DS-B-G4 prepared in example 2, the oligonucleotides ON1 are deposited in the 0.3M phosphate buffer (pH 9) using the deposition robot. The volumes deposited are 2 nl and the concentration is 10 µM. After deposition, the slides are left overnight at room temperature. They are then immersed in aqueous sodium borohydride solution (NaBH$_4$, 3.5 mg/ml) (step of reduction of the imine functions) and are agitated for 3 hours at room temperature. They are rinsed with MilliQ water (3 washes of 5 minutes each) and are dried under a stream of nitrogen or by centrifugation. Dendrichips DC1-B-G4 are obtained.

The oligonucleotides ON2 were also deposited on the dendrislides prepared in example 2.

To do this, the oligonucleotides ON2 are deposited in MilliQ water. The volumes deposited are 0.2 µl and the concentrations range from 1 µM to 10 µM (1 µM, 5 µM and 10 µM).

On the same slide, the oligonucleotides ON1 were deposited in the 0.3M phosphate buffer under the same volume and concentration conditions. The slides are left for 7 hours at room temperature. They are then immersed in aqueous sodium borohydride solution (NaBH$_4$, 3.5 mg/ml) and are agitated for 3 hours at room temperature. They are then rinsed with MilliQ water (1 wash of 5 minutes), with aqueous 0.2% sodium dodecyl sulfate (SDS) solution (1 wash of 5 minutes) and again with water (5 minutes). They are finally dried under a stream of nitrogen. Dendrichips DC2-B-G4 are obtained.

Various kinds of biochips corresponding to dendrislides to which oligonucleotides have been bound ("dendrichips") are thus obtained. These dendrichips may then be used in hybridization reactions.

EXAMPLE 4

Hybridization

1) Materials and Methods 1-a) Buffers Used
The various buffers used during the hybridization steps are reported below; they were prepared from the following various commercial solutions:
20×SSC (0.3M sodium citrate; 3M NaCl, pH about 7; sigma)
20×SSPE (0.2M phosphate buffer, 2.98M NaCl, 0.02M EDTA, pH about 7.4; sigma),
50× Denhardt's solution (sigma),
salmon DNA (9.9 mg/ml, sigma).

Hybridization buffer: SSPE 2×, 0.1% SDS [target ON]=200 nM, pH 7.4 with, as target oligonucleotides:

ON-Cy5: 5' - Cy5—AAT GGT ATC GGA GTA - 3'

ON-Cy3: 5' - Cy3—AAT GGT ATC GGA GTA - 3'

The sequence of these target oligonucleotides corresponds to sequence SEQ ID No 2
Washing buffer: SSPE 2×, 0.1% SDS, pH 7.4:
Dehybridization buffer: 2.5 mM Na$_2$HPO$_4$, 0.1% SDS 1-b) Hybridization Step
The hybridizations are performed by adding the required amount of labeled targets (from 2 µl to 40 µl depending on the surface area to be covered) to the deposition area of each dendrichip.

Various concentrations of targets to be detected: 200 nM, 100 nM, 20 nM, 10 nM, 2 nM and 1 nM were prepared and used during the hybridization steps in order to evaluate the detection sensitivity of the dendrichips in accordance with the invention.

The drop is then covered with a cover slip and the assembly is placed in a hybridization chamber (CMT hybridization chamber sold by the company Corning). The slides are left for 15 minutes at room temperature and are then washed using the washing buffer for 5 minutes at room temperature. They are finally dried under a stream of nitrogen.

1-c) Reading of the Slides
The slides are read using an Axon scanner equipped with two lasers allowing reading at excitation wavelengths of 532 nm and 635 nm (Cy3 and Cy5, respectively). The fluorescence emitted by the fluorochromes after excitation is detected by a photomultiplier to be (PMT). Conventionally, the PMT has a value of between 450 and 600. The result is obtained in the form of an image file with a resolution of 10 m/pixel. Computer analysis of the image files and quantification of the fluorescence intensity were performed using the Genepix® software.

1-d) Dehybridization Step

When the reading of the slides is complete, the slides are dehybridized.

To do this, the dendrichips are placed in a 50 ml flask tube filled with the dehybridization buffer described above. The assembly is maintained at 95° C. for 5 minutes. The slide is then rinsed three times with MilliQ water and dried by centrifugation or under a stream of nitrogen. The slide is then scanned in order to ensure that dehybridization has indeed taken place. It is thus ready to be used again for another hybridization.

1-e) Study of Mutations

Depositions:

The oligonucleotide ON1 as described above (10 µM, 2 nl) is deposited on the dendrislides DS-A-G3, DS-A-G4 or DS-A-G5 prepared according to example 1. The depositions are performed at four different points on the same dendrislide. The hybridizations are performed using four oligonucleotides 15 bases long functionalized at their 5' ends with a fluorophore Cy5, and which contain the four possible bases T, A, G or C in the middle of the sequence (Eurogentec). The sequences of these oligonucleotides are as follows:

- "15mer Cy5 T" (complementary):
  5' - Cy5–AAT GGT ATC GGA GTA 3'     (SEQ ID No 2)

- "15mer Cy5 A":
  5' - Cy5–AAT GGT AAC GGA GTA 3'     (SEQ ID No 3)

- "15mer Cy5 G":
  5' - Cy5–AAT GGT AGC GGA GTA 3'     (SEQ ID No 4)

- "15mer Cy5 C":
  5' - Cy5–AAT GGT ACC GGA GTA 3'     (SEQ ID No 5)

Hybridizations

Hybridization buffer: SSC 6×, 0.2% SDS, 5× Denhardt's solution, 10 µg salmon DNA, pH 7 containing the 15mer oligonucleotide Cy5 T, A, G or C at a concentration of 200 nM.

washing buffer: wash 1: SSC 2×, 0.1% SDS, pH 7
wash 2: SSC 0.2×.

5 µl of each of the hybridization solutions are deposited on each deposition area consisting of oligonucleotide ON1. Each area is covered with a cover slip (without the cover slips touching each other). The slide is placed in a hybridization chamber (Corning), which is immersed in a bath at 42° C. for 1 hour. The slides are then washed with the washing buffer 1 for 5 minutes at room temperature or at 50° C., and then with the washing buffer 2 for 5 minutes at 50° C. They are finally dried under a stream of nitrogen.

2) Results 2-a) Reuse of the Dendrichips and Detection Sensitivity as a Function of the Nature of the Deposition Buffer, of the ON Concentration and of the Nature of the Dendrimers On the dendrichips DC1-A-G3, DC1-A-G4 and DC1-A-G5, and for each test concentration of targets to be detected, the hybridization, slide reading and dehybridization steps were performed 7 times with the 15-mer ON Cy5 (200 nM), in order to demonstrate the reusable nature of the dendrichips in accordance with the invention, and also the sensitivity and reproducibility of the results obtained. The fluorescence intensity values are collated in tables II to IV below; the PMT has a value of 600 and the depositions were performed in triplicate for each buffer:

TABLE II

| Concentration ON1: 5 µM | | | Concentration ON1: 10 µM | | |
|---|---|---|---|---|---|
| Concentration DMSO (%) | Diameter of the deposits (µm) | Signal/noise | Concentration DMSO (%) | Diameter of the deposits (µm) | Signal/noise |
| DC1-A-G3: AFTER THE FIRST HYBRIDIZATION | | | | | |
| 0 | 90 | 65000/200 | 0 | 100 | 65000/200 |
| 10 | 110 | 65000/200 | 10 | 110 | 65000/200 |
| 20 | 110 | 65000/200 | 20 | 140 | 65000/200 |
| 30 | 140 | 65000/200 | 30 | 140 | 65000/200 |
| 40 | 140 | 65000/200 | 40 | 150 | 65000/200 |
| 50 | 160 | 42000/200 | 50 | 160 | 50000/200 |
| AFTER SEVEN HYBRIDIZATIONS | | | | | |
| 0 | 90 | 65000/300 | 0 | 100 | 65000/350 |
| 10 | 110 | 65000/300 | 10 | 110 | 65000/350 |
| 20 | 110 | 65000/300 | 20 | 140 | 65000/350 |
| 30 | 140 | 65000/300 | 30 | 140 | 65000/350 |
| 40 | 140 | 65000/300 | 40 | 150 | 65000/350 |
| 50 | 160 | 50000/300 | 50 | 160 | 50000/350 |

TABLE III

| Concentration ON1: 5 μM | | | Concentration ON1: 10 μM | | |
|---|---|---|---|---|---|
| Concentration DMSO (%) | Diameter of the deposits (μm) | Signal/noise | Concentration DMSO (%) | Diameter of the deposits (μm) | Signal/noise |
| DC1-A-G4: AFTER THE FIRST HYBRIDIZATION | | | | | |
| 0 | 90 | 65000/300 | 0 | 100 | 65000/300 |
| 10 | 120 | 65000/300 | 10 | 110 | 65000/300 |
| 20 | 120 | 53000/300 | 20 | 110 | 65000/300 |
| 30 | 140 | 65000/300 | 30 | 170 | 65000/300 |
| 40 | 160 | 65000/300 | 40 | 190 | 65000/300 |
| 50 | 170 | 53000/200 | 50 | 180 | 65000/200 |
| AFTER SEVEN HYBRIDIZATIONS | | | | | |
| 0 | 90 | 65000/300 | 0 | 100 | 65000/350 |
| 10 | 110 | 65000/300 | 10 | 110 | 65000/350 |
| 20 | 110 | 56000/300 | 20 | 140 | 45000/350 |
| 30 | 140 | 52000/300 | 30 | 140 | 65000/350 |
| 40 | 140 | 65000/300 | 40 | 150 | 65000/350 |
| 50 | 160 | 48000/300 | 50 | 160 | 51000/350 |

TABLE IV

| Concentration ON1: 5 μM | | | Concentration ON1: 10 μM | | |
|---|---|---|---|---|---|
| Concentration DMSO (%) | Diameter of the deposits (μm) | Signal/noise | Concentration DMSO (%) | Diameter of the deposits (μm) | Signal/noise |
| DC1-A-G5: AFTER THE FIRST HYBRIDIZATION | | | | | |
| 0 | 100 | 65000/200 | 0 | 90 | 65000/200 |
| 10 | 110 | 65000/200 | 10 | 100 | 65000/200 |
| 20 | 130 | 65000/200 | 20 | 120 | 45000/200 |
| 30 | 160 | 38000/200 | 30 | 170 | 65000/200 |
| 40 | 170 | 65000/200 | 40 | 180 | 65000/200 |
| 50 | 180 | 47000/200 | 50 | 170 | 48000/200 |
| AFTER SEVEN HYBRIDIZATIONS | | | | | |
| 0 | 90 | 65000/500 | 0 | 100 | 65000/500 |
| 10 | 110 | 65000/500 | 10 | 110 | 65000/500 |
| 20 | 110 | 56000/500 | 20 | 140 | 45000/500 |
| 30 | 140 | 52000/500 | 30 | 140 | 65000/500 |
| 40 | 140 | 60000/500 | 40 | 150 | 62000/500 |
| 50 | 160 | 42000/500 | 50 | 160 | 60000/500 |

These results show that the signal/noise ratios are virtually constant between the first and the seventh hybridization. These results demonstrate that the dendrichips in accordance with the invention may be reused without any reduction in the signal/noise ratio.

Furthermore, these results show that the signal/noise ratios obtained with the various buffer concentrations are very similar and thus indicative of the reproducibility and sensitivity of the measurements.

Similarly, 10 hybridization and dehybridization cycles were performed on the dendrichips DC1-B-G4 as prepared above in example 2.

Figure 5:
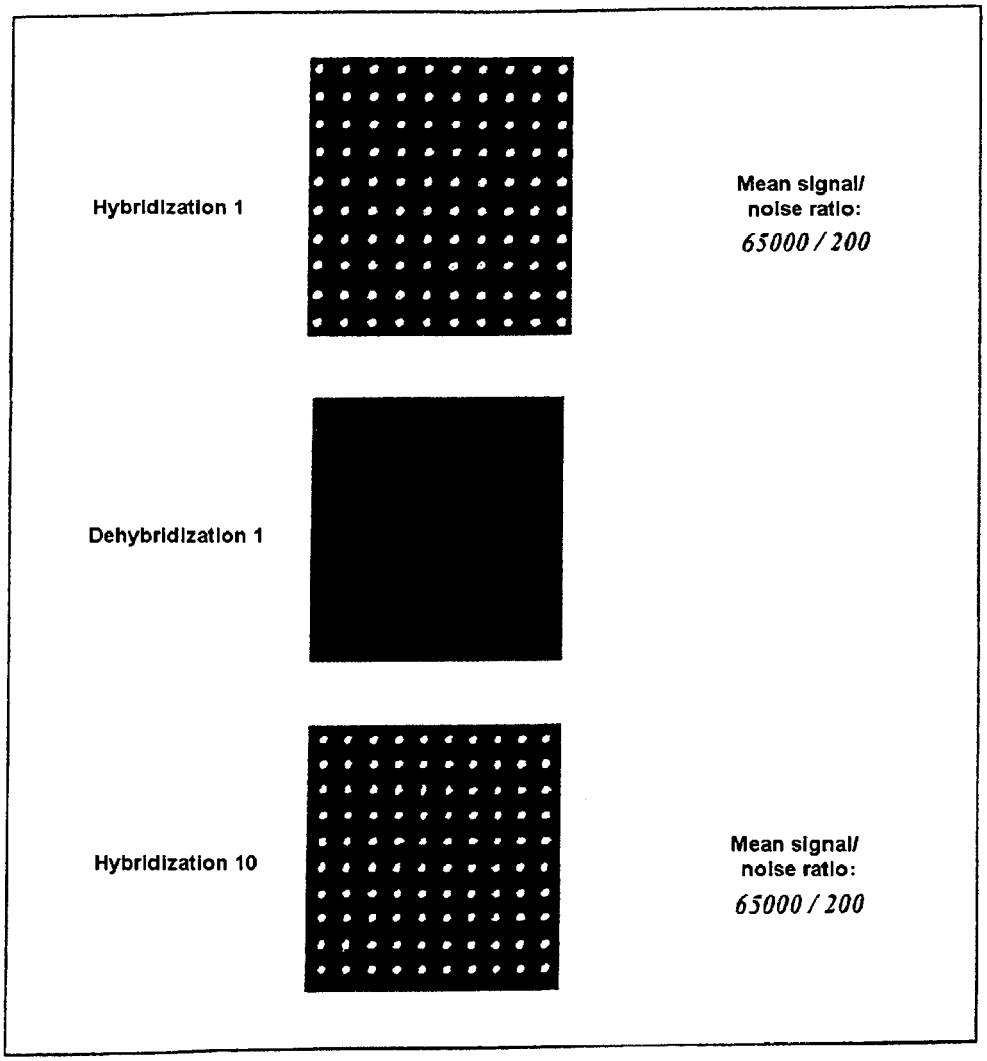
FIG. 5 shows images of the fluorescence signals obtained after 10 hybridization/dehybridization cycles on dendrichips in accordance with the invention.

The results obtained, in the form of images of the fluorescence signals, are given in FIG. 5.

These results show that the signal/noise ratio after the first hybridization (65000/200) is the same after the tenth hybridization and thus indicative of the reusable nature of the dendrichips in accordance with the present invention.

2-b) Reuse of the Dendrichips and Detection Sensitivity as a Function of the Concentration of Target ON and of the Nature of the Dendrimers The oligonucleotide ON1 was deposited at five different points onto the dendrichips DC1-A-G3, DC1-A-G4 and DC1-A-G5 as prepared in example 3 above.

The following hybridization solutions containing decreasing concentrations of target ON-Cy5 were used in order to evaluate the sensitivity of the dendrichips in accordance with the invention:

SSPE 2×, SDS 0.1%, [ON-Cy5]=200 nM
SSPE 2×, SDS 0.1%, [ON-Cy5]=100 nM
SSPE 2×, SDS 0.1%, [ON-Cy5]=20 nM
SSPE 2×, SDS 0.1%, [ON-Cy5]=10 nM
SSPE 2×, SDS 0.1%, [ON-Cy5]=2 nM
SSPE 2×, SDS 0.1%, [ON-Cy5]=1 nM

2 μl of each of these hybridization solutions were deposited on the dendrichips and left to incubate for 15 minutes at room temperature. The dendrichips were then washed with the SSPE 2×, 0.1% SDS buffer for 5 minutes at room temperature, and then dried under a stream of nitrogen or by centrifugation. 10 hybridization/dehybridization cycles were thus performed.

Figure 6:
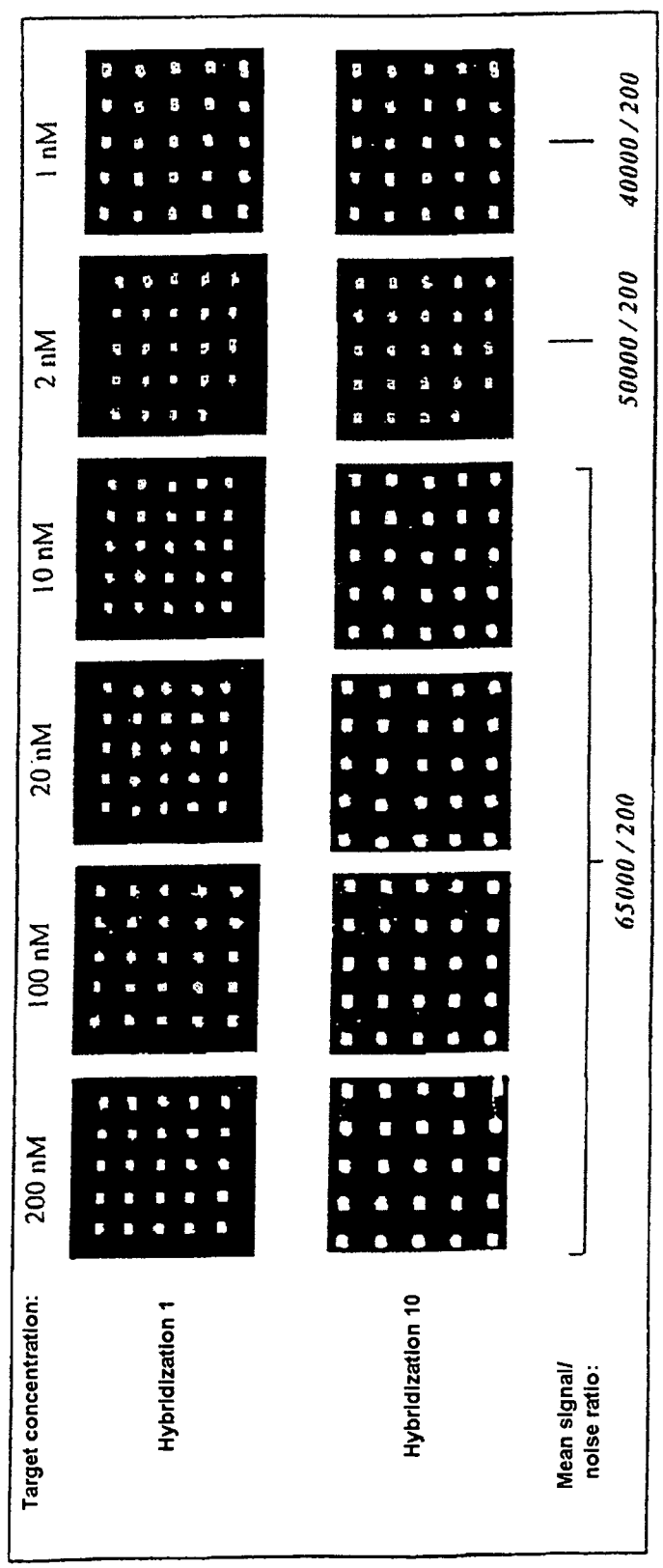
FIG. 6 shows images of the fluorescence signals obtained after 10 cycles of hybridization/dehybridization on dendrichips in accordance with the invention as a function of the concentration of target oligonucleotides.

The images obtained are given in FIG. 6.

These results show that for a concentration of target ON-Cy5 ranging between 200 nM and 10 nM, and even after 10 hybridization/dehybridization cycles, a constant signal/noise ratio of 65 000/200 is obtained. For a lower concentration of target ON-Cy5, i.e. of 2 nM or 1 nM, signal/noise ratios of 50 000/200 and 40 000/200, respectively, are obtained, which are indicative of the very good detection sensitivity of the dendrichips in accordance with the invention and the reproducibility of the results that they make it possible to obtain when they are reused several times.

2-b) Detection of Mutations

Figure 7:
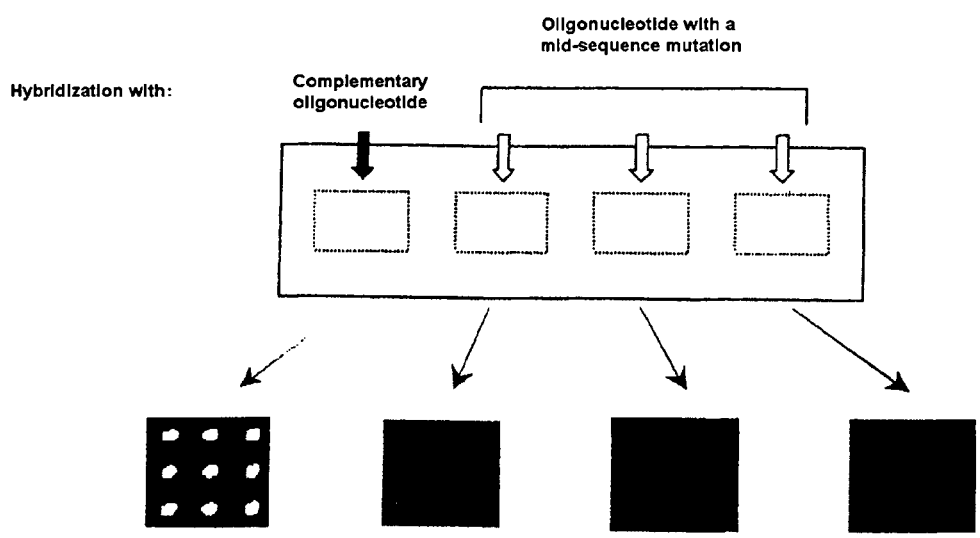
FIG. 7 shows images of the fluorescence signals obtained during a study concerning the search for mutations on oligonucleotides.

The results obtained are presented on the attached FIG. 7, on which it may be seen that only the perfectly complementary oligonucleotide leads to production of a fluorescence signal, whereas no fluorescence signal is obtained with the oligonucleotides containing a mid-chain mutation. The dendrichips in accordance with the invention thus make it possible to detect mutations.

EXAMPLE 5

Synthesis of a Third Generation Dendrimer Containing Thiol End Groups

1) First Step: Synthesis of a Third Generation Dendrimer Containing NH(Me) End Groups A slight excess of monomethyl hydrazine (224 µl) is added, by syringe, to a solution of third generation dendrimer ($N_3P_3$ core, Launay et al, cited hereinabove) containing aldehyde end groups (650 mg) in dichloromethane. After stirring for 4 hours at room temperature, the reaction medium is concentrated under reduced pressure and the third generation dendrimer containing NH(Me) end groups is then precipitated using diethyl ether (3×15 ml). The resulting white powder is washed several times with this solvent, and then dried under reduced pressure.

2) Second Step: Synthesis of a Third Generation Dendrimer Containing Thiol End Groups The third generation dendrimer containing NH(Me) end groups obtained in step 1) above (1 g) is dissolved in 2.5 ml of γ-thiobutyrolactone in a Schlenk tube. The mixture is stirred for 3 days at 50-55° C. under autogenous pressure. After cooling, the crude reaction mixture is washed with 3×50 ml of diethyl ether to give a third generation dendrimer containing 48 thiol functions at its periphery.

Figure 3:
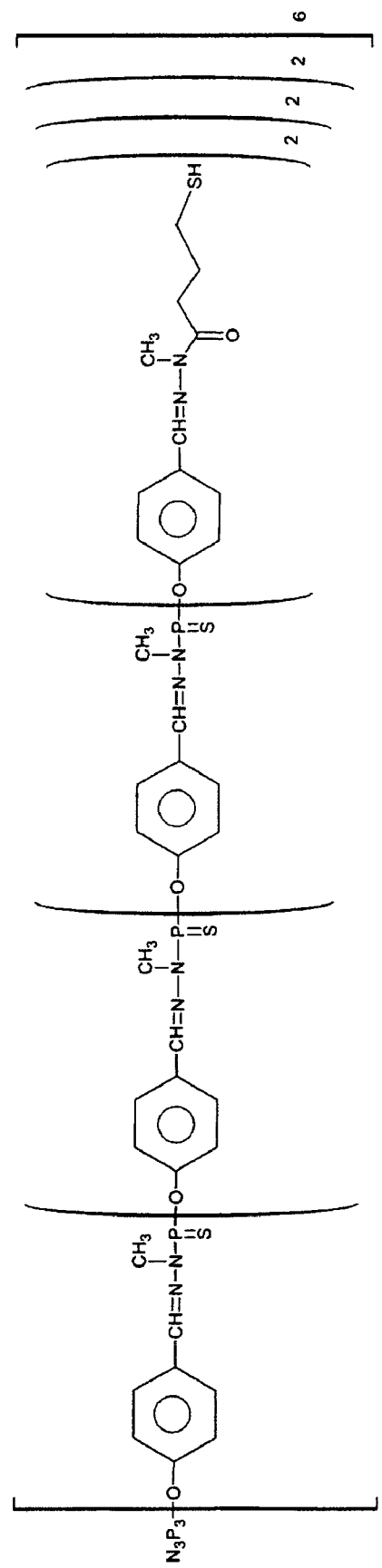
FIG. 3 is the formula of a third generation phosphorus-containing dendrimer containing thiol-terminal peripheral functions.
Figure 3:
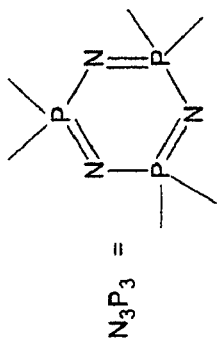
Figure 4:
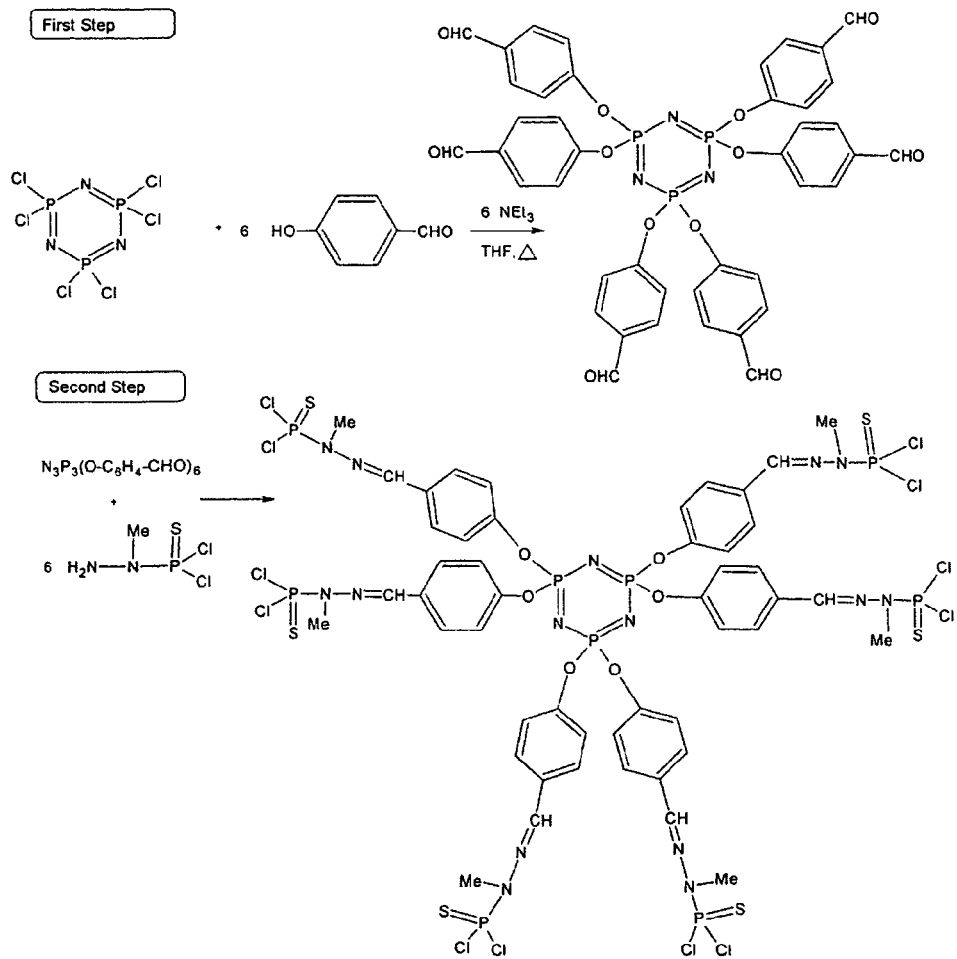
FIG. 4 is a synthetic scheme A showing the first two steps of the process for preparing a dendrimer with a phosphorus-containing core.

This dendrimer, which is presented in the attached FIG. 3, may then be used for the manufacture of the dendrislides in accordance with the invention. Comment: This procedure is general and allows dendrimers of any generation containing thiol end groups to be obtained (Schmid et al., Chem. Eur. J., 2000, 6, 1693).

EXAMPLE 6

Preparation of "Dendrislides" Functionalized with Dendrimers Containing Thiol End Groups $SiO_2$, silanized $SiO_2$ or SiNx slides on which are mounted gold terminals (10 µm$^2$ to 500 µm$^2$) are prewashed with 95% ethanol and dried with compressed air. They are then immersed for variable times (15 minutes, 1 hour, 2 hours and 12 hours) in a solution consisting of 100 µg of third generation dendrimers containing thiol end groups as prepared above in example 5, dissolved in 5 ml of distilled THF. The slides are then washed with distilled THF (±ultrasound), and then with ethanol, after which they are dried with compressed air. The result of the grafting (not shown) is observed by atomic force microscopy (AFM). In the case of the gold terminals on the $SiO_2$ support, the grafting of the G3-thiol dendrimers is non-selective (binding both to the gold and to the $SiO_2$ support). In the case of the silanized $SiO_2$ or SiNx supports, the grafting of the G3-thiol dendrimers takes place selectively on the gold terminals. Silicon/gold slides whose surface is functionalized with third generation thiol-dendrimers (dendrislides: DS-C-G3') are thus obtained. These dendrislides may then be used for the immobilization of molecules of interest.

The invention claimed is:

1. A solid support, comprising at least one surface covalently functionalized with phosphorus-containing dendrimers having a central core that contains at least two functional groups and comprising at their periphery several functions binding said dendrimers to said surface and also allowing the binding or the in situ synthesis of molecules of interest, said dendrimers being between 1 and 20 nm in size, characterized in that the dendrimers are chosen from those consisting of:

a central layer in the form of a central core $P_0$, optionally containing phosphorus, comprising from 2 to 12 functionalized groups, n intermediate layers, which may be identical or different, each of said intermediate layers consisting of $P_1$ units corresponding to formula (I) below:

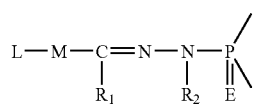

(I)

in which:

L is an oxygen, phosphorus, sulfur or nitrogen atom,

M represents one of the following groups:

an aromatic group di-, tri- or tetrasubstituted with alkyl groups, alkoxy groups, unsaturated groups of the $C_1$-$C_{12}$ olefinic, azo or acetylenic type, all these groups possibly incorporating phosphorus, oxygen, nitrogen or sulfur atoms or halogens, or an alkyl or alkoxy group comprising several substituents as defined when M is an aromatic group, $R_1$ and $R_2$, which may be identical or different, represent a hydrogen atom or one of the following groups: alkyl, alkoxy, aryl, optionally comprising phosphorus, oxygen, sulfur or nitrogen atoms or halogens with $R_2$ usually being different than $R_1$, n is an integer between 1 and 11, E is an oxygen, sulfur or nitrogen atom, said nitrogen atom possibly being linked to an alkyl, alkoxy or aryl group, all these groups possibly incorporating phosphorus, oxygen, nitrogen or sulfur atoms or halogens, an external layer consisting of units $P_2$, which may be identical or different, and corresponding to formula II below:

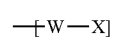

(II)

in which:

W represents one of the following groups: alkyl, alkoxy, aryl, all these groups possibly comprising phosphorus, oxygen, nitrogen or sulfur atoms or halogens, X represents an aldehyde, thiol, amine, epoxide, carboxylic acid, alcohol or phenol group.

2. The solid support as claimed in claim 1, characterized in that the central core $P_0$ is selected from the group consisting of the group of general formula IIIa:

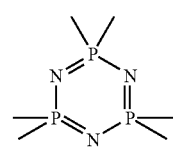

(IIIa)

and the group of general formula IIIb:

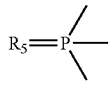
(IIIb)

in which $R_5$ represents a sulfur, oxygen or nitrogen atom.

3. The support as claimed in claim 1, characterized in that the dendrimers are chosen from compounds in which the group of formula (I) represents the following group:

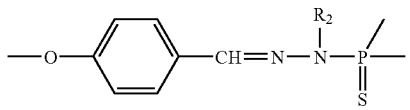

in which $R_2$ represents a $C_1$-$C_{12}$ alkyl radical and more particularly a methyl radical;

and the group of formula (II) represents one of the following two groups:

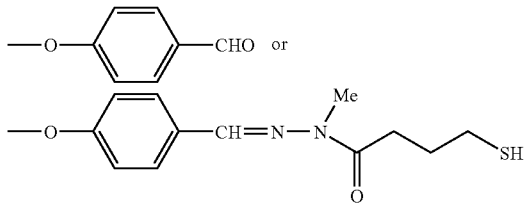

and in which the number of generations preferably ranges between 1 and 6.

4. The solid support as claimed in claim 1, characterized in that it is chosen from supports comprising at least one siliceous surface, such as glass slides, beads and capillaries, silicon or plastic supports and metallic supports.

5. A process for preparing a solid support as defined in claim 1, characterized in that it comprises a step of forming a covalent bond between phosphorus-containing dendrimers having a central core that contains at least two functional groups, said dendrimers comprising at their periphery several functions capable of allowing their binding to said surface and the binding or the in situ synthesis of molecules of interest, and the functionalized or nonfunctionalized surface of a solid support to obtain a solid support covalently functionalized with said dendrimers.

6. The process as claimed in claim 5, characterized in that the dendrimers comprise at their periphery functions allowing the direct attachment, via a covalent bond, of these dendrimers to the non-prefunctionalized surface of said solid support.

7. The process as claimed in claim 6, characterized in that the dendrimers comprise thiol functions at their periphery and in that the solid support comprises a gold surface.

8. The process as claimed in claim 5, in which the surface of the solid support used does not comprise any functions that are compatible with the peripheral functions of the dendrimer used, characterized in that it comprises the following steps:
   a) the functionalization of at least one surface of a solid support with functions capable of allowing the binding of phosphorus-containing dendrimers having a central core that contains at least two functional groups, said dendrimers comprising at their periphery several functions capable of allowing their binding to said surface thus functionalized and the binding or the in situ synthesis of molecules of interest;
   b) the optional preactivation of the functions of the support to obtain an activated functionalized surface,
   c) the formation of a covalent bond between said dendrimers and said functionalized and optionally activated surface, to obtain a solid support covalently functionalized with said dendrimers.

9. The process as claimed in claim 8, characterized in that the step a) of functionalization of the surface of the solid support is performed by silanization using a silanization reagent comprising functions capable of binding dendrimers, for instance amine groups.

10. The process as claimed in claim 8, characterized in that the silanization reagent is aminated.

11. The process as claimed in claim 8, characterized in that the preactivation step is performed by treating the support with a basifying agent for a period of between 2 and 20 minutes.

12. Process according to claim 5, characterized in that the step of covalent binding of the dendrimers consists in:
   preparing a solution of said dendrimers in a solvent,
   placing said dendrimer solution in contact with the optionally functionalized and optionally activated surface, for a period of between 10 minutes and 24 hours.

13. The process as claimed in-claim 5, characterized in that after the step of covalent binding of the dendrimers, the supports are rinsed and then dried.

14. A process for the immobilization and/or in situ synthesis of molecules of interest comprising providing a solid support functionalized with phosphorus-containing dendrimers as defined in claim 1, and binding and/or in situ synthesizing the molecules of interest at said functions of said support.

15. The process as claimed in claim 14, characterized in that the molecules of interest are nucleic acid molecules, lipids, proteins or molecular partners thereof.

* * * * *

UNITED STATES PATENT AND TRADEMARK OFFICE
CERTIFICATE OF CORRECTION

PATENT NO. : 7,517,538 B2
APPLICATION NO. : 10/512133
DATED : April 14, 2009
INVENTOR(S) : Trevisiol et al.

It is certified that error appears in the above-identified patent and that said Letters Patent is hereby corrected as shown below:

On the Title page,

Item (*) Notice: Cancel "This patent is subject to a terminal disclaimer.".

Signed and Sealed this

Thirtieth Day of June, 2009

JOHN DOLL
*Acting Director of the United States Patent and Trademark Office*

SEQUENCE LISTING

<160> NUMBER OF SEQ ID NOS: 5

<210> SEQ ID NO 1
<211> LENGTH: 35
<212> TYPE: DNA
<213> ORGANISM: Saccharomyces cerevisiae

<400> SEQUENCE: 1
gtgatcgttg tatcgaggaa tactccgata ccatt      35

<210> SEQ ID NO 2
<211> LENGTH: 15
<212> TYPE: DNA
<213> ORGANISM: Artificial Sequence
<220> FEATURE:
<223> OTHER INFORMATION: oligonucleotide

<400> SEQUENCE: 2
aatggtatcg gagta      15

-continued

```
<210> SEQ ID NO 3
<211> LENGTH: 15
<212> TYPE: DNA
<213> ORGANISM: Artificial Sequence
<220> FEATURE:
<223> OTHER INFORMATION: Oligonucleotide

<400> SEQUENCE: 3
aatggtaacg gagta                                                   15

<210> SEQ ID NO 4
<211> LENGTH: 15
<212> TYPE: DNA
<213> ORGANISM: Artificial Sequence
<220> FEATURE:
<223> OTHER INFORMATION: Oligonuclotide

<400> SEQUENCE: 4
aatggtagcg gagta                                                   15

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide

<400> SEQUENCE: 5
aatggtaccg gagta                                                   15
```